United States Patent [19]
Genova et al.

[11] Patent Number: 6,008,261
[45] Date of Patent: Dec. 28, 1999

[54] AQUEOUS SURFACTANT COMPOSITIONS WITH A HIGH VISCOSITY

[75] Inventors: Calogero Genova, Vizzolo Predabissi; Filippo Montesion, Gropello; Edy Bozzeda, Milan, all of Italy

[73] Assignee: Condea Augusta S.p.A., Palermo, Italy

[21] Appl. No.: 08/848,191

[22] Filed: Apr. 29, 1997

[30] Foreign Application Priority Data

May 3, 1996 [IT] Italy .................................. MI96A0866

[51] Int. Cl.⁶ .............................. B01F 17/00; C11D 1/02; C11D 1/94

[52] U.S. Cl. ........................... 516/58; 510/535; 510/536; 510/126; 510/130; 510/237; 424/70.19; 516/70; 516/73; 516/909; 516/918

[58] Field of Search ............................. 252/354; 516/58, 516/64, 70, 73, 74, 75, 909, 913, 918, 920; 510/535, 536, 126, 127, 130, 138, 235, 237; 424/70.19, 70.21, 70.24, 70.31

[56] References Cited

U.S. PATENT DOCUMENTS

| | | | |
|---|---|---|---|
| 4,834,970 | 5/1989 | Login et al. | 424/70.28 |
| 5,002,680 | 3/1991 | Schmidt et al. | 510/140 |
| 5,352,387 | 10/1994 | Rahman et al. | 510/496 |
| 5,366,665 | 11/1994 | Cho | 424/65 |
| 5,407,678 | 4/1995 | Rose et al. | 424/401 |
| 5,612,307 | 3/1997 | Chambers et al. | 510/130 |

FOREIGN PATENT DOCUMENTS

| | | |
|---|---|---|
| 1 314 616 | 4/1973 | United Kingdom . |
| WO 95/05153 | 2/1995 | WIPO . |

OTHER PUBLICATIONS

"Derwent Publications Ltd.", Database WPI, Week 7948, London, Oct. 1979, p. 1 Japanese Abstract JP 54 134 711 A (Lion Fat & Oil KK), Oct. 19, 1979.

"Derwent Publications Ltd.", Database WPI, Week 9252, London, Nov. 1992, p. 1 Japanese Abstract JP 04 323 299 A (Kao Corp.), Nov. 12, 1992.

*Primary Examiner*—Richard D. Lovering
*Assistant Examiner*—Daniel S. Metzmaier
*Attorney, Agent, or Firm*—Oblon, Spivak, McClelland, Maier & Neustadt, P.C.

[57] ABSTRACT

Aqueous surfactant compositions, with a high viscosity, comprising an anionic surfactant or a mixture of anionic surfactants, an alkyl ester of lactic acid or a mixture of alkyl esters of lactic acid and, optionally, an electrolyte. The above compositions can be used for the preparation of liquid detergents, either transparent or translucent, opaque or pearly, for use as "personal care" products, domestic detergents, car detergents.

1 Claim, No Drawings

AQUEOUS SURFACTANT COMPOSITIONS WITH A HIGH VISCOSITY

The present invention relates to aqueous surfactant compositions with a high viscosity.

More specifically, the present invention relates to aqueous surfactant compositions, with a high viscosity, comprising an anionic surfactant or a mixture of anionic surfactants, an alkyl ester of lactic acid or a mixture of alkyl esters of lactic acid and, optionally, an electrolyte.

A further object of the present invention relates to the use of these compositions for the preparation of liquid detergents, transparent or translucent, opaque or pearly, as "personal care" products such as, for example, shampoo, bath-foam, shower-gel, liquid cleansers for face and body, domestic detergents such as, for example, dishwashing liquid detergent, liquid detergent for delicate hand-washing, and car detergents such as, for example, shampoo for car-washing.

Aqueous surfactant compositions with a high viscosity are, in many cases, preferred to those with a low viscosity as these compositions are simpler to handle and the dosage is easier. If the composition contains a second phase (solid or liquid) the high viscosity also gives a higher stability to storage.

In addition, aqueous surfactant compositions with a high viscosity are of interest to the market as the consumer often associates low viscosity preparations with a low concentration of active matter.

Aqueous surfactant compositions often contain anionic surfactants such as, for example, fatty alcohol ethoxy-sulfates, fatty alcohol sulfates, fatty alcohol sulfosuccinates, alkane sulfonates or ethoxycarboxylic acids, as main component, sometimes in the presence of other compounds such as, for example, betaine, amphoteric compounds or alkanolamides of fatty acids. In the case of fatty alcohol ethoxy-sulfates and fatty alcohol sulfates, a simple increase of the viscosity can be obtained by adding inorganic salts soluble in water (electrolytes) such as, for example, NaCl, $NH_4Cl$ and $Na_2SO_4$. The quantity of electrolyte, however, which is necessary for adequately viscosizing the aqueous surfactant compositions can be rather high, further increasing the already marked irritating power on the skin and mucous membranes of compositions of anionic surfactants. Many other surfactants which are of particular interest for use in the above compositions, as they are not very irritating for the skin and mucous membranes, cannot easily and economically produce however aqueous compositions with a high viscosity.

Alkanolamides of fatty acids can be used as viscosity regulators but even these are undesirable as the low content of free alkanolamine can cause in the end-product the formation of nitrosamine as by-product. Consequently, as specified by H. Hensen et al, in "2nd World Surfactant Congress" (1988), Paris, Vol. II, page 378, additives not containing nitrogen are preferred.

Saturated or unsaturated oxyethylated fatty alcohols having a low degree of ethoxylation, preferably containing 2.5 moles of ethylene oxide per mole of product (EO moles/mole), are a solution to the above problem but even these, however, are not advantageous as they have a high fat-dissolving capacity and their limited solubility in water reduces their foaming capacity.

Other thickening agents which are efficient apart from the surfactants used, belong to the group of polymers soluble in water. For this purpose, useful agents are derivatives of cellulose and xanthanes. Other useful agents are, for example, derivatives of polyethylene glycol (DE 3.140.160), polyol monoethers (EP 303.187), polyoxyalkylene ethers of glycerol or propano-1,2-diol esterified with fatty acids (DE 3.239.564) or other polyhydroxylic alcohols (DE 3.843.224) and alkylpolyethylene glycolethers esterified with fatty acids (DE 3.541.813). The thickening action of these agents is presumably due to the highly hydrated cross-link which is formed and which is capable of partially immobilizing water. In this case, there is, at times, a certain synergism between the surfactant and the polymer but the concentration of polymer required to obtain the desired viscosity value is so high, that the final aqueous composition is relatively costly. The use of polymers such as those containing polyethyleneglycol is debatable also from an ecological point of view as these polymers are not biodegradable.

In addition, owing to the high concentration of polymer, there are drawbacks during processing and at times unsatisfactory rheological characteristics. The above polymers should therefore only be added to cosmetic compositions in small quantities.

German patent DE 3.843.224 describes a surfactant composition containing a non-ionic surfactant with a low degree of ethoxylation and a polymer but, also in this case, there are problems both of an ecological and toxic nature, as these products are not well tolerated by the skin and mucous membranes.

There is therefore the necessity of obtaining an aqueous surfactant composition with a high viscosity, using thickening agents which do not have the disadvantages described above.

The Applicant has now found that it is possible to overcome the above drawbacks of the known art, thanks to the use of esters of lactic acid or their mixtures, as thickening agents.

Esters of lactic acid are already widely used in the cosmetic industry as emollient oils with dermatological properties such as, for example, anti-acne, keratolytic, moisturizing and anti-aging action. These esters, although practically insoluble in water, can be very easily solubilized in water systems of mixtures of surfactants to obtain perfectly limpid and stable solutions even at temperatures of less than 0° C. The aqueous surfactant compositions thus obtained have the following advantages:

they can be more easily viscosized and therefore the presence of electrolytes which, when present, are in any case used in low quantities, is not always necessary;

they have an equivalent foaming capacity, if not better in some cases, with respect to the corresponding compositions obtained without the ester of lactic acid;

they remain transparent even at low temperatures;

they are less aggressive than the corresponding compositions obtained without the ester of lactic acid and are consequently well tolerated by the skin and mucous membranes.

The use of the above esters, thanks to their dermatological properties, gives the final aqueous surfactant compositions a delicacy which is difficult to find in commercial compositions. The velvet touch of the end-product and the softness of hands even after prolonged contact with the detergent aqueous solution, is definitely linked to the reduced irritating capacity of the end-product containing the ester of lactic acid and this anti-irritating characteristic, is not common in detergent products.

Clinical tests also show that the use of esters of lactic acid, and in particular of Cosmacol ELI (which is described hereunder), enables a considerable reduction in the irritating effect of anionic surfactants, particularly of alkylsulfate or alkylethoxysulfate products.

The present invention therefore relates to aqueous surfactant compositions, with a high viscosity, comprising:
(a) 4%–50% by weight of an anionic surfactant or a mixture of anionic surfactants;
(b) 0.1%–10% by weight of an alkyl ester of lactic acid or a mixture of alkyl esters of lactic acid having general formula (I):

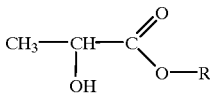  (I)

wherein R represents a $C_4$–$C_{20}$ alkyl group, linear or branched; an aryl group having general formula (II):

  (II)

wherein R' represents a $C_4$–$C_{20}$ alkyl group, linear or branched; an alkylethoxylic group having general formula (III)

  (III)

wherein R" represents a $C_4$–$C_{20}$ alkyl group, linear or branched and n is an integer or an average number from 1 to 20;
(c) 0%–2.5% of an electrolyte;
the complement to 100 consisting of water.

The aqueous surfactant compositions, with a high viscosity, of the present invention preferably comprise:
(a) 5%–35% by weight of an anionic surfactant or mixture of anionic surfactants;
(b) 0.2%–5% by weight of an alkyl ester of lactic acid or a mixture of alkyl esters of lactic acid having general formula (I):

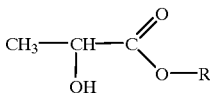  (I)

wherein R represents a $C_4$–$C_{20}$ alkyl group, linear or branched; an aryl group having general formula (II):

  (II)

wherein R' represents a $C_4$–$C_{20}$ alkyl group, linear or branched; an alkylethoxylic group having general formula (III):

  (III)

wherein R" represents a $C_4$–$C_{20}$ alkyl group, linear or branched and n is an integer or fraction of between 1 and 20 extremes included;

(c) 0%–2% of an electrolyte;
the complement to 100 consisting of water.

Anionic surfactants (a) useful for the purposes of the present invention are fatty alcohol ethoxy-sulfates, fatty alcohol sulfates, fatty alcohol carboxymethylates oxyethylates, fatty alcohol sulfosuccinates, fatty alcohol ethoxy-sulfosuccinates, alkanes sulfonated, alkylbenzenes sulfonated, salts of fatty acids, alkyl betaines, or their mixtures. In the above surfactants the length of the saturated or unsaturated chain, linear or branched, is, in each case, from 8 to 22 carbon atoms, preferably from 10 to 20 carbon atoms and the cations are $Na^+$, $K^+$, $NH_4^+$, $C_2$-$C_3$-alkanolammonium or $Mg^{2+}$. The degrees of ethoxylation are between 1 and 5, preferably between 2 and 4 EO moles/mole, in the case of fatty alcohol ethoxy-sulfates; between 2 and 15, preferably between 3 and 10 EO moles/mole, in the case of fatty alcohol carboxymethylates oxyethylates; between 1 and 6, preferably between 2 and 4 EO moles/mole, in the case of fatty alcohol ethoxy-sulfosuccinates.

Preferred for the purposes of the present invention are: fatty alcohol ethoxy-sulfates, for this purpose ($C_{12}$-$C_{15}$)-Pareth-3 sulfate (aqueous solution at 27% of active matter) and ($C_{12}$-$C_{15}$)-Pareth-2 sulfate (aqueous solution at 27% of active matter), sold by Condea Augusta S.p.a., were used; alkyl betaines, for this purpose Coccoamidopropylbetaine sold by Condea Augusta S.p.A. was used; fatty alcohol ethoxy-sulfosuccinates, for this purpose ($C_{12}$-$C_{15}$)-Pareth-3 sulfosuccinate in its salified form (bisodic salt; aqueous solution at 35% of active matter) sold by Condea Augusta S.p.A., was used, or their mixtures.

A specific example of an alkyl ester (b) useful for the purposes of the present invention is lauryl-lactate wherein R, in general formula (I), is a linear alkyl group containing 12 carbon atoms. For this purpose Ceraphyl 31, sold by Van Dyk, was used. Ceraphyl 31 is obtained by the esterification of lactic acid with lauryl alcohol.

A specific example of a mixture of alkyl esters of lactic acid (b) is a mixture of alkyl esters of lactic acid wherein R, in general formula (I), represents a monobranched alkyl group containing from 12 to 13 carbon atoms. For this purpose Cosmacol ELI, sold by Condea Augusta S.p.A. was used. Cosmacol ELI is obtained by the esterification of lactic acid with a mixture of monobranched primary $C_{12}$–$C_{13}$ alcohols, obtained by the oxo-alcohol process, known by the name of Isalchem, sold by Condea Augusta S.p.a.

Electrolytes (c) which can possible be added to the aqueous surfactant compositions of the present invention, are electrolytes soluble in water such as, for example, halides, sulfates or phosphates of alkaline metals, halides, sulfates or phosphates of ammonium and halides, sulfates or phosphates of earth-alkaline metals.

The preferred electrolyte (c) for the purpose is sodium chloride (NaCl).

The aqueous surfactant compositions of the present invention, depending on their final use, can also contain other compounds such as, for example, silicon surfactants, hydrolyzed proteins, humectants, preservatives, plant extracts, buffers, complexing agents, perfumes.

The aqueous surfactant compositions of the present invention are generally used for the preparation of liquid detergents, transparent or translucent, opaque or pearly, as "personal care" products, for example, shampoo, bath-foam, shower-gel, liquid cleansers for the face and body, as domestic detergent products such as, for example, dishwashing liquid detergent, liquid detergent for hand-washing, and as car detergents such as, for example, shampoo for car washing.

For the purposes of the present invention, two basic mixtures were prepared for "personal care" products (DL 1.0 and BS 1.0) varying the concentration of the mixture of anionic surfactants as shown in Table 1. The above mixtures were prepared by the simple mixing, at room temperature, of the components indicated in Table 1.

TABLE 1

| COMPONENTS | COMPOSITIONS (weight %) | |
|---|---|---|
| | DL 1.0 | BS 1.0 |
| Cosmacol AES 327 (1) | 30.0 | 50.0 |
| Cosmacol BT35 (2) | 5.0 | 5.0 |
| Demineralized $H_2O$ | 64.8 | 44.5 |
| EDTA (disodic salt) (3) | 0.15 | 0.15 |
| Gram 1 (4) | 0.15 | 0.15 |
| Perfume (5) | 0.20 | 0.50 |

(1): ($C_{12}$—$C_{15}$)-Pareth-3 sulfate (aqueous solution at 27% of active matter);
(2): Coccoamidopropylbetaine (aqueous solution at 35% of active matter);
(3): Sodium ethylenediaminotetracetate (bisodic salt), sold by Fluka S.p.A.;
(4): Preservative sold by Sinerga S.p.A.;
(5): Perfume: Code number PINO 79265/SMA distributed by Variati S.p.A.

From the above basic mixtures, the aqueous surfactant compositions shown in Table 2 were subsequently prepared. These compositions are prepared at room temperature by the simple addition, at low stirring rate, in one case, of alkanolamide from coconut acid (CoccoDEA) to prepare classical formulations for "personal care" products and, in the other case, of the ester of lactic acid (Ceraphyl 31) or the mixture of esters of lactic acid (Cosmacol ELI).

TABLE 2

| COMPONENTS | COMPOSITIONS (weight %) | | | | | | | | |
|---|---|---|---|---|---|---|---|---|---|
| | DL 2.0 | DL 3.0 | DL D2.0 | DL D3.0 | BS 2.0 | BS 4.0 | BS D2.0 | BS D4.0 | BS Cr.0 |
| DL 1.0 | 99.5 | 99.0 | 99.5 | 99.0 | — | — | — | — | — |
| Cosmacol ELI | 0.5 | 1.0 | — | — | 1.0 | 1.5 | — | — | — |
| CoccoDEA | — | — | 0.5 | 1.0 | — | — | 1.0 | 1.5 | — |
| BS 1.0 | — | — | — | — | 99.0 | 98.5 | 99.0 | 98.5 | 99.0 |
| Ceraphyl 31 | — | — | — | — | — | — | — | — | 1.0 |

The compositions indicated in Table 2 will be used in the following examples to show the viscosizing ability of the esters of lactic acid or mixtures of esters of lactic acid.

An electrolyte (NaCl) will, in fact, be subsequently added to the compositions indicated in Table 2, at a concentration varying from 0% to 4%, as specified in the following examples. All the compositions were prepared, also in this case, by gentle stirring at room temperature. For all the samples, the rheological behaviour was determined, using a roto-viscometer (of the type Haake VT500) thermostat-regulated at 25° C. for at least 30 minutes, by monitoring the viscosity with the variation of the applied shear-rate (flow curve). Independently from the concentration of the anionic surfactant and type of system examined, it was observed that, whereas without or with a low concentration of electrolyte the samples have a Newtonian behaviour (viscosities constant with an increase in the applied shear-rate), by increasing the concentration of electrolyte the rheological behaviour changes radically becoming pseudoplastic (reduction of the viscosities with an increase in the applied shear-rate).

To compare the various systems examined, the following tables indicate the viscosity values of the various samples tested with the same applied shear-rate.

Please refer to Tables 1 and 2 for explanations of the abbreviations of the compositions indicated in the Tables.

The following illustrative examples are given to provide a better understanding of the present invention and for its embodiment but in no way restrict the scope of the invention itself.

EXAMPLE 1

NaCl is added to the compositions indicated in Tables 1 and 2 and the viscosity is registered, operating as described above. The results obtained are shown in Table 3.

TABLE 3

| NaCl | Viscosity (mPa/s) (shear-rate = 10.8 l/s) | | |
|---|---|---|---|
| (weight %) | DL 1.0 | DL 2.0 | DL D2.0 |
| 0 | 2.7 | 2.5 | 2.3 |
| 0.25 | — | — | — |
| 0.5 | — | — | — |
| 1.0 | 4 | 40 | 40 |
| 1.5 | — | 410 | 230 |
| 2.0 | 40 | 1470 | 1950 |
| 2.5 | 320 | 3180 | 2470 |
| 3.0 | 930 | 5720 | 5490 |
| 4.0 | 4210 | — | — |

The aqueous surfactant compositions, without the electrolyte and in the presence of viscosizing agents at a concentration equal to 0.5% with respect to the total of the mass (DL 2.0 and DL D2.0), have very low viscosity values, similar to the viscosity value found in the basic aqueous surfactant composition DL 1.0 (without electrolyte and viscosizing agents) and equivalent among them.

The addition of the electrolyte (NaCl) on the other hand causes a change in behaviour: in fact, the aqueous surfactant compositions containing the viscosizing agent (DL 2.0 and DL D2.0) are more easily viscosized with respect to the basic solution (DL 1.0). It should also be noted that there are no substantial differences in behaviour between the compositions containing Cosmacol ELI (DL 2.0) and those containing CoccoDEA (DL D2.0).

EXAMPLE 2

NaCl is added to the compositions indicated in Tables 1 and 2 and the viscosity is registered, operating as described above. The results obtained are shown in Table 4.

TABLE 4

| NaCl | Viscosity (mPa/s) (shear-rate = 10.8 l/s) | | |
|---|---|---|---|
| (weight %) | DL 1.0 | DL D3.0 | DL 3.0 |
| 0 | 2.7 | 3.1 | 8.1 |
| 0.25 | — | — | 40 |
| 0.5 | — | 15 | 390 |
| 1.0 | 4 | 150 | 1500 |
| 1.5 | — | 1500 | 2890 |
| 2.0 | 40 | 4380 | 3600 |
| 2.5 | 320 | — | — |
| 3.0 | 930 | 6670 | — |
| 4.0 | 4210 | — | — |

The aqueous surfactant compositions, without electrolyte and in the presence of viscosizing agents at a concentration equal to 1% with respect to the total of the mass (DL 3.0 and DL D3.0), have very low viscosity values and equivalent among them.

The addition of the electrolyte (NaCl) on the other hand brings a change in behaviour: in fact, in the aqueous surfactant composition containing Cosmacol ELI (DL 3.0), the increase in viscosity by the addition of small quantities of NaCl is remarkably more significant than that observed in the aqueous surfactant composition containing CoccoDEA (DL D3.0).

EXAMPLE 3

NaCl is added to the compositions indicated in Tables 1 and 2 and the viscosity is registered, operating as described above. The results obtained are shown in Table 5.

TABLE 5

| NaCl | Viscosity (mPa/s) (shear-rate = 10.8 l/s) | | | |
|---|---|---|---|---|
| (weight %) | BS 1.0 | BS 2.0 | BS D2.0 | BS CR.0 |
| 0 | 4 | 20 | 5 | 10 |
| 0.25 | 8 | 100 | 10 | 50 |
| 0.5 | 15 | 320 | 15 | 200 |
| 1.0 | 25 | 1050 | 250 | 1960 |
| 1.5 | 200 | 5800 | 1620 | 5600 |
| 2.0 | 1470 | 11500 | 8000 | 10500 |
| 2.5 | 5800 | — | — | — |
| 3.0 | 5740 | — | 12700 | — |

The aqueous surfactant compositions, without electrolyte and in the presence of Cosmacol ELI and Ceraphyl 31 at a concentration equal to 1% with respect to the total of the mass (BS 2.0 and BS CR.0), have higher viscosity values than those observed in the aqueous surfactant composition containing CoccoDEA (BS D2.0).

The addition of the electrolyte (NaCl), causes easier viscosization in the case of aqueous solutions of surfactants containing Cosmacol ELI (BS 2.0) or Ceraphyl 31 (BS Cr.0), already in the presence of small quantities of NaCl. This viscosization facility is remarkably higher than that observed in the aqueous surfactant composition containing CoccoDEA (BS D2.0).

A comparison between the rheological behaviour of the aqueous surfactant compositions containing the two different esters of lactic acid (Cosmacol ELI or Ceraphyl 31) shows that the two have an essentially equivalent behaviour.

EXAMPLE 4

NaCl is added to the compositions indicated in Tables 1 and 2 and the viscosity is registered, operating as described above. The results obtained are shown in Table 6.

TABLE 6

| NaCl | Viscosity (mPa/s) (shear-rate = 10.8 l/s) | | |
|---|---|---|---|
| (weight %) | BS 1.0 | BS 4.0 | BS D4.0 |
| 0 | 4 | 200 | 11 |
| 0.25 | 8 | 1000 | 50 |
| 0.5 | 15 | 4000 | 160 |
| 1.0 | 25 | 5570 | 370 |
| 1.5 | 200 | 9980 | 2480 |
| 2.0 | 1470 | 11700 | 4460 |
| 2.5 | 5800 | — | 7210 |
| 3.0 | 5740 | — | — |

The aqueous surfactant compositions without electrolyte and in the presence of viscosizing agents at a concentration equal to 1.5% with respect to the total of the mass, have high viscosity values in the case of the aqueous surfactant composition containing Cosmacol ELI (BS 4.0), low in the case of the basic aqueous surfactant composition BS 1.0 (without electrolyte and viscosizing agent) and in the case of the aqueous surfactant composition containing CoccoDEA (BS D4.0).

The addition of the electrolyte (NaCl) causes easier viscosization in the case of the aqueous composition containing Cosmacol ELI (BS 4.0), already in the presence of small quantities of NaCl; this behaviour is maintained for the whole range of NaCl concentration. This viscosization facility is remarkably higher than that observed in the aqueous composition containing CoccoDEA (BS D4.0).

EXAMPLE 5

Aqueous surfactant compositions were prepared using a fatty alcohol ethoxysulfosuccinate having 3 EO moles/mole. For this purpose $C_{12}$-$C_{15}$-Pareth-3 sulfosuccinate was used in its salified form (bisodic salt; aqueous solution at 35% of active matter), mixed with other anionic surfactants.

The components are mixed as described above and the results obtained from the viscosity registrations (carried out as described above) are shown in Table 7.

TABLE 7

| | COMPOSITIONS (weight %) | | | | | |
|---|---|---|---|---|---|---|
| COMPONENTS | AD.25 | AD.5 | AD.1 | AE.25 | AE.5 | AE.1 |
| Cosmacol AES 227(1) | 40.0 | 40.0 | 40.0 | 40.0 | 40.0 | 40.0 |
| Cosmacol BT 35(2) | 5.0 | 5.0 | 5.0 | 5.0 | 5.0 | 5.0 |
| Cosmacol LSS(3) | 10.0 | 10.0 | 10.0 | 10.0 | 10.0 | 10.0 |

TABLE 7-continued

| COMPONENTS | COMPOSITIONS (weight %) | | | | | |
|---|---|---|---|---|---|---|
| | AD.25 | AD.5 | AD.1 | AE.25 | AE.5 | AE.1 |
| Cosmacol DEA(4) | 1.0 | 1.0 | 1.0 | — | — | — |
| Cosmacol ELI | — | — | — | 1.0 | 1.0 | 1.0 |
| Perfume(5) | 0.5 | 0.5 | 0.5 | 0.5 | 0.5 | 0.5 |
| Demin. H₂O | 43.0 | 42.5 | 42.0 | 43.0 | 42.5 | 42.0 |
| Gram 1(6) | 0.25 | 0.25 | 0.25 | 0.25 | 0.25 | 0.25 |
| EDTA (disodic salt) | 0.25 | 0.25 | 0.25 | 0.25 | 0.25 | 0.25 |
| NaCl | 0.25 | 0.5 | 1.0 | 0.25 | 0.5 | 1.0 |
| Viscosity (mPa/s) (shear-rate = 10.8 1/s) | 100 | 500 | 2000 | 1500 | 8500 | 14000 |

(1)($C_{12}$–$C_{13}$)-Pareth-2 sulfate (aqueous solution at 27% of active matter);
(2)Coccoamidopropylbetaine (aqueous solution at 35% of active matter);
(3)$C_{12}$–$C_{15}$-Pareth-3 sulfosuccinate (bisodic salt; aqueous solution at 35% of active matter);
(4)CoccoDEA;
(5)Perfume: GNS Dragogo cod. 0/232774 distributed by Dragogo S.p.A.;
(6)Preservative, sold by Sinerga S.p.A.

As can be seen from the results indicated in Table 7, the aqueous surfactant compositions containing Cosmacol ELI (AE.25, AE.5 and AE.1) are much more viscous with respect to the corresponding compositions containing CoccoDEA (AD.25, AD.5 and AD.1).

EXAMPLE 6
Evaluation of foaming capacity

The foaming capacity of the aqueous surfactant compositions prepared as described in Examples 1 and 4, was determined by the Ross-Miles method, operating at 30° C. and diluting the samples to a concentration of 2 g/l both with demineralized water and with water containing $CaCl_2$ at a concentration corresponding to a hardness of 30° F.

The concentration of 2 g/l was reached considering as active matter all the components except the perfume, preservative and EDTA. The experimental results are shown in Table 8.

TABLE 8

| | Demineralized water | | | Hard H₂O 30° F. | | |
|---|---|---|---|---|---|---|
| Monogram Time | 0.00 | 30 sec. | 5 min. | 0.00 | 30 sec. | 5 min. |
| | Foam height (mm) | | | | | |
| DL 1.0 | 165 | 155 | 150 | 190 | 170 | 165 |
| DL 3.0 | 175 | 155 | 150 | 175 | 155 | 150 |
| DL D3.0 | 185 | 165 | 160 | 205 | 185 | 180 |
| BS 1.0 | 170 | 150 | 145 | 185 | 165 | 155 |
| BS 2.0 | 160 | 140 | 135 | 180 | 160 | 150 |
| BS D2.0 | 175 | 155 | 150 | 195 | 175 | 165 |
| BS CR.0 | 155 | 140 | 130 | 175 | 160 | 150 |
| BS 4.0 | 160 | 140 | 135 | 180 | 160 | 150 |
| BS D4.0 | 175 | 155 | 150 | 195 | 175 | 165 |

From the results shown in Table 8 it can be observed that, among the compositions tested, there is no substantial difference in the foaming capacity without or in the presence of the ester of lactic acid or mixture of esters of lactic acid.

EXAMPLE 7
Evaluation of storage stability

Small amounts of each single composition prepared as described in Examples 1–4 are placed in well-closed test-tubes thermostat-regulated in a Haake cryostat. The initial observation temperature was set at 10° C. and observation was made after 24 hours of thermostat-regulation. The experimental results relating to the minimum temperature at which the samples maintain their transparent appearance (storage stability) are shown in Table 9.

TABLE 9

| | NaCl concentration (% w/w) | | | | | | |
|---|---|---|---|---|---|---|---|
| | 0 | 0.5 | 1.0 | 1.5 | 2.0 | 2.5 | 3.0 |
| Monogram | Temperature (° C.) | | | | | | |
| DL 1.0 | −2.0 | — | −1.0 | 2.0 | 5.0 | 5.0 | 5.0 |
| DL 2.0 | −1.0 | — | −1.0 | −2.0 | −1.0 | −1.0 | — |
| DL D2.0 | −8.0 | — | −6.0 | −6.0 | −4.0 | −4.0 | — |
| DL 3.0 | −8.0 | −6.0 | — | — | — | — | — |
| DL D3.0 | −8.0 | −6.0 | −6.0 | −4.0 | −4.0 | — | −2.0 |
| BS 1.0 | 5.0 | 5.0 | 5.0 | 5.0 | 5.0 | 5.0 | 5.0 |
| BS 2.0 | −3.0 | −2.0 | −1.0 | −1.0 | −1.0 | — | — |
| BS D2.0 | −1.0 | 0 | 2.0 | 2.0 | 2.0 | — | 2.0 |
| BS CR.0 | 5.0 | 5.0 | 7.0 | 7.0 | 7.0 | — | — |
| BS 4.0 | −4.0 | −2.0 | −2.0 | −2.0 | −2.0 | — | — |
| BS D4.0 | 0 | 2.0 | 2.0 | 2.0 | 2.0 | — | — |

From the values showned in Table 9 it can be seen that both the addition of Cosmacol ELI and the addition of CoccoDEA enable an improvement in the stability of the aqueous surfactant compositions of the present invention allowing the transparency (storage stability) to be maintained at a lower temperature with respect to the compositions prepared without them.

In addition, for high concentrations of surfactants, the presence of Cosmacol ELI, even at concentrations of 1.5% (BS 4.0) renders the samples transparent also at temperatures lower than 0° C., as the corresponding samples containing CoccoDEA (BS D4.0), are transparent only at temperatures higher than 0° C. and the samples containing Ceraphyl 31 (BS CR.0) are transparent at higher temperatures than those registered by testing the corresponding samples prepared with the basic aqueous surfactant composition (BS 1.0).

The distinct difference in behaviour between Cosmacol ELI and Ceraphyl 31 shows the importance of the branched molecular structure of the hydrophobic portion of Cosmacol ELI with respect to the linear structure of Ceraphyl 31.

We claim:

1. Aqueous surfactant compositions consisting of:
    (a) 4%–50% by weight of an anionic surfactant, alkyl betaines or mixtures thereof;

(b) 0.1%–10% by weight of an alkyl ester of lactic acid or a mixture of alkyl esters of lactic acid having the formula (I):

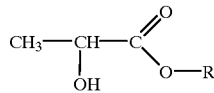
(I)

wherein R represents a $C_4$–$C_{20}$ alkyl group, linear or branched; an aryl group having the formula (II):

(II)

wherein R' represents a $C_4$–$C_{20}$ alkyl group, linear or branched; an alkylethoxylic group having the formula (III):

$$R''-(-O-CH_2-CH_2-)_n- \qquad (III)$$

wherein R'' represents a $C_6$–$C_{20}$ alkyl group, linear or branched and n is an integer or an average number from 1 to 20;

(c) 0%–2.5% by weight of an electrolyte;

the complement to 100% by weight consisting of water.

* * * * *

UNITED STATES PATENT AND TRADEMARK OFFICE
CERTIFICATE OF CORRECTION

PATENT NO. : 6,008,261
DATED : December 28, 1999
INVENTOR(S) : Calogero GENOVA et al.

It is certified that error appears in the above-identified patent and that said Letters Patent is hereby corrected as shown below:

On the title page, item [45], is incorrectly listed. It should be:

--[45] Date of Patent: *Dec. 28, 1999--

After item [73], please insert:

--[*] Notice: This patent issued on a continued prosecution application filed under 37 CFR 1.53(d), and is subject to the twenty year patent term provisions of 35 U.S.C. 154(a)(2).--

Signed and Sealed this

Twenty-third Day of January, 2001

Attest:

Q. TODD DICKINSON

*Attesting Officer*  *Commissioner of Patents and Trademarks*